United States Patent [19]

König et al.

[11] Patent Number: 5,686,421
[45] Date of Patent: Nov. 11, 1997

[54] HYDANTOIN DERIVATES

[75] Inventors: Wolfgang König, Hofheim am Taunus; Melitta Just, Langen; Bernd Jablonka, Bad Soden am Taunus, all of Germany

[73] Assignee: Hoechst Aktiengesellschaft, Frankfurt am Main, Germany

[21] Appl. No.: 467,526

[22] Filed: Jun. 6, 1995

Related U.S. Application Data

[63] Continuation of Ser. No. 673,512, Mar. 22, 1991, abandoned.

[30] Foreign Application Priority Data

Mar. 24, 1990 [DE] Germany .................... 40 09 506.1

[51] Int. Cl.$^6$ .................... A61K 38/04; C07K 5/00
[52] U.S. Cl. .................... 514/18; 514/19; 530/330; 530/331; 548/319.5
[58] Field of Search .................... 514/18, 19; 530/330, 530/331; 548/319.5

[56] References Cited

U.S. PATENT DOCUMENTS

| | | | |
|---|---|---|---|
| 4,578,079 | 3/1986 | Ruoslahti et al. | 530/330 |
| 4,614,517 | 9/1986 | Ruoslahti et al. | 530/330 |
| 4,683,291 | 7/1987 | Zimmerman et al. | 530/327 |
| 5,389,614 | 2/1995 | Konig et al. | 514/18 |

FOREIGN PATENT DOCUMENTS 0341915  11/1989  European Pat. Off. .

OTHER PUBLICATIONS

B. Schwenzer et al., "Cleavage of Z–Group and Formation of Hydantoin During Alkaline Saponification of Z–Peptide Esters," Chemical Abstracts, 103:215779s (1985).

Fruton et al., J. Biol. Chem., vol. 145, pp. 253–265 (1942).
Dekker et al., J. Biol. Chem., vol. 180, pp. 155–173 (1949).
Cox et al., J. Chem. Soc., vol. 23, pp. 6806–6313 (1965).
Pless, J. Org. Chem., vol. 39, No. 17, pp. 2644–2646 (1974).
Davies et al., J. Chem. Soc. Perkin Trans. I, pp. 2939–2947 (1982).
Ruoslahti et al., Science, vol. 238, pp. 491–497 (1987).
Phillips et al., J. Amer. Soc. Hem., Blood, vol. 71, No. 4, pp. 831–843 (1988).
Pierschbacher et al., Nature, vol. 309, pp. 30–33 (1984).
Pierschbacher et al., J. Biol. Chem., vol. 262, No. 36, pp. 17294–17298 (1987).
Charon et al., Amer. Peptide Symp., pp. 82–83 (1989).

*Primary Examiner*—Cecilia J. Tsang
*Assistant Examiner*—Bennett Celsa
*Attorney, Agent, or Firm*—Finnegan, Henderson, Farabow, Garrett & Dunner, L.L.P.

[57] ABSTRACT

Hydantoin derivatives of the formula I

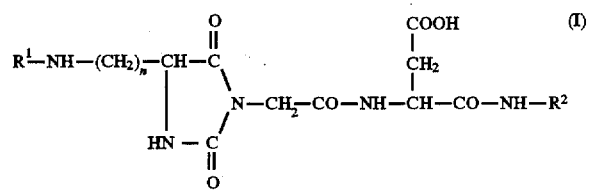

in which n is 3 or 4, $R^1$ is alkyl or a radical of the formula R'—NH—C=N—R" with R' and R" being hydrogen or alkyl, and $R^2$ is hydrogen, —NH—CO—NH$_2$ and optionally substituted alkyl, and a process for the preparation thereof and the use thereof for inhibiting platelet aggregation, are described.

13 Claims, No Drawings

HYDANTOIN DERIVATES

This application is a continuation of application Ser. No. 07/673,512, filed Mar. 22, 1991, now abandoned.

The invention relates to novel hydantoin derivatives with a platelet antiaggregant-action.

The invention relates to compounds of the formula I

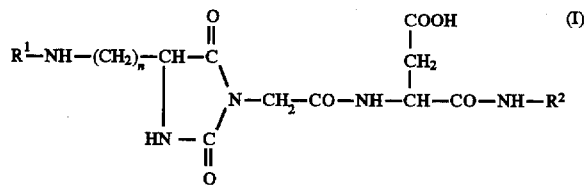

in which n is an integer 3 or 4;

$R^1$ is $C_1$–$C_6$-alkyl or a radical of the formula II

in which

R' and R" are, independently of one another, hydrogen or $C_1$–$C_6$-alkyl;

$R^2$ is hydrogen, —NH—CO—NH$_2$ or $C_1$–$C_{18}$-alkyl which is optionally substituted one or more times by identical or different radicals from the series comprising hydroxyl, carboxyl, carbamoyl, carboxamido, amino, mercapto, $C_1$–$C_{18}$-alkoxy, guanidino, $C_3$–$C_8$-cycloalkyl, halogen, nitro, trifluoromethyl and a radical $R^3$, where $R^3$ is $C_6$–$C_{14}$-aryl, $C_6$–$C_{14}$-aryl-$C_1$–$C_8$-alkyl or a mono- or bicyclic 5- to 12-membered heterocyclic ring which can be aromatic, partially hydrogenated or completely hydrogenated and which can contain as hetero element one, two or three identical or different nitrogen, oxygen or sulfur atoms, where the aryl and, independently of one another, the heterocyclic radical is optionally substituted one or more times by identical or different radicals from the series comprising $C_1$–$C_{18}$-alkyl, hydroxyl, $C_1$–$C_{18}$-alkoxy, halogen, nitro and trifluoromethyl; or is a radical $R^4$; where $R^4$ is $NR^5R^6$; $OR^5$; $SR^5$; an amino-acid side-chain; a residue of a natural or unnatural amino acid, imino acid, optionally N—$C_1$–$C_8$-alkylated or $C_6$–$C_{14}$-aryl-$C_1$–$C_8$-alkylated azaamino acid or a dipeptide in which the peptide linkage can be reduced to NH—CH$_2$, and the esters and amides thereof, where free functional groups can optionally be replaced by hydrogen or hydroxymethyl or protected by the protective groups customary in peptide chemistry; or is a radical $COR^{4'}$ in which $R^{4'}$ is defined as $R^4$;

$R^5$ is hydrogen, optionally amino group-substituted $C_1$–$C_{18}$-alkyl, $C_6$–$C_{14}$-aryl, $C_6$–$C_{14}$-aryl-$C_1$–$C_8$-alkyl, $C_1$–$C_{18}$-alkylcarbonyl, $C_1$–$C_{18}$-alkyloxycarbonyl, $C_6$–$C_{14}$-arylcarbonyl, $C_6$–$C_{12}$-aryl-$C_1$–$C_8$-alkylcarbonyl, $C_6$–$C_{18}$-aryl-$C_1$–$C_{18}$-alkyloxycarbonyl, a residue of a natural or unnatural amino acid, imino acid, optionally N—$C_1$–$C_8$-alkylated or $C_6$–$C_{14}$-aryl-$C_1$–$C_8$-alkylated azaamino acid or a dipeptide in which the peptide linkage can be reduced to NH—CH$_2$;

$R^6$ is hydrogen, $C_1$–$C_{18}$-alkyl, $C_6$–$C_{12}$-aryl or $C_6$–$C_{12}$-aryl-$C_1$–$C_8$-alkyl;

and the physiologically tolerated salts thereof.

Alkyl can be straight-chain or branched. A corresponding statement applies to radicals derived therefrom such for example, alkoxy, alkanoyl and aralkyl.

Cycloalkyl also means alkyl-substituted radicals such as, for example, 4-methylcyclohexyl or 2,3-dimethylcyclopentyl. $C_6$–$C_{14}$-aryl is, for example, phenyl, naphthyl, biphenylyl or fluorenyl; phenyl and naphthyl are preferred. A corresponding statement applies to radicals derived therefrom such as, for example, aryloxy, aroyl, aralkyl and aralkoxy. Aralkyl means, for example, an unsubstituted or substituted $C_6$–$C_{14}$-aryl radical which is linked to $C_1$–$C_8$-alkyl, such as, for example, benzyl, 1- and 2-naphthylmethyl, halobenzyl and alkoxybenzyl, but with aralkyl not being restricted to the said radicals.

Examples of heterocycles within the meaning of the present definitions are pyrrolyl, furyl, thienyl, imidazolyl, pyrazolyl, oxazolyl, isoxazolyl, thiazolyl, isothiazolyl, tetrazolyl, pyridyl, pyrazinyl, pyrimidinyl, indolyl, isoindazolyl, indazolyl, phthalazinyl, quinolyl, isoquinolyl, quinoxalinyl, quinazolinyl, cinnolinyl or a benzo-fused, cyclopenta-, cyclohexa- or cyclohepta-fused derivative of these radicals.

These heterocycles can be substituted on one nitrogen atom by oxides, $C_1$–$C_7$-alkyl, for example methyl or ethyl, phenyl or phenyl-$C_1$–$C_4$-alkyl, for example benzyl, and/or on one or more carbon atoms by $C_1$–$C_4$-alkyl, for example methyl, phenyl, phenyl-$C_1$–$C_4$-alkyl, for example benzyl, halogen, hydroxyl, $C_1$–$C_4$-alkoxy, for example methoxy, phenyl-$C_1$–$C_4$-alkoxy, for example benzyloxy, or oxo and be partially or completely saturated.

Examples of radicals of this type are 2- or 3-pyrrolyl, phenyl-pyrrolyl, for example 4- or 5-phenyl-2-pyrrolyl, 2-furyl, 2-thienyl, 4-imidazolyl, methylimidazolyl, for example 1-methyl-2-, 4- or 5-imidazolyl, 1,3-thiazol-2-yl, 2-, 3- or 4-pyridyl, 2-, 3- or 4-pyridyl N-oxide, 2-pyrazinyl, 2-, 4-or 5-pyrimidinyl, 2-, 3-, or 5-indolyl, substituted 2-indolyl, for example 1-methyl-, 5-methyl-, 5-methoxy-, 5-benzyloxy-, 5-chloro- or 4,5-dimethyl-2-indolyl, 1-benzyl-2- or 3-indolyl, 4,5,6,7-tetrahydro-2-indolyl, cyclohepta [b]-5-pyrrolyl, 2-, 3- or 4-quinolyl, 1-, 3- or 4-isoquinolyl, 1-oxo-1,2-dihydro-3-isoquinolyl, 2-quinoxalinyl, 2-benzofuranyl, 2-benzothienyl, 2-benzoxazolyl or benzothiazolyl. Examples of partially hydrogenated or completely hydrogenated heterocyclic rings are dihydropyridinyl, pyrrolidinyl, for example 2-, 3- or 4-N-methylpyrrolidinyl, piperazinyl, morpholino-, thiomorpholino, tetrahydrothienyl and benzodioxolanyl.

Halogen is fluorine, chlorine, bromine or iodine, especially fluorine or chlorine.

Natural or unnatural amino acids can, if chiral, be in the D or L form. α-Amino acids are preferred. Examples which may be mentioned are (cf. Houbèn-Weyl, Methoden der organischen Chemie [Methods of Organic Chemistry], volume XV/1 and 2, Stuttgart, 1974):

Aad, Abu, TAbu, ABz, 2ABz, εAca, Ach, Acp, Adpd, Ahb, Aib, βAib, Ala, βAla, ΔAla, Alg, All, Ama, Amt, Ape, Apm, Apr, Arg, Asn, Asp, Asu, Aze, Azi, Bai, Bph, Can, Cit, Cys, (Cys)$_2$, Cyta, Daad, Dab, Dadd, Dap, Dapm, Dasu, Djen, Dpa, Dtc, Fel, Gln, Glu, Gly, Guy, hAla, hArg, hCys, hGln, hGlu, His, hIle, hLeu, hLys, hMet, hPhe, hPro, hSer, hThr, hTrp, hTyr, Hyl, Hyp, 3Hyp, Ile, Ise, Ira, Kyn, Lant, Lcn, Leu, Lsg, Lys, βLys, ΔLys, Met, Mim, Min, nArg, Nle, Nva, Oly, Orn, Pan, Pec, Pen, Phe, Phg, Pic, Pro, ΔPro, Pse, Pya, Pyr, Pza, Qin, Ros, Sat, Sec, Sem, Ser, Thi, βThi, Thr, Thy, Thx, Tia, Tle, Tly, Trp, Trta, Tyr, Val, Tbg, Npg, Chg, Cha, Thia, 2,2-diphenylaminoacetic acid, 2-(p-tolyl)-2-phenylaminoacetic acid and 2-(p-chlorophenyl)aminoacetic acid.

Amino-acid side-chains means side-chains of natural or unnatural amino acids. Azaamino acids are natural or unnatural amino acids where the central —CHR— or —CH$_2$— unit is replaced by —NR— or —NH—.

Particularly suitable as radical of an imino acid are radicals of heterocycles from the following group:

Pyrrolidine-2-carboxylic acid; piperidine-2-carboxylic acid; tetrahydroisoquinoline-3-carboxylic acid; decahydroisoquinoline-3-carboxylic acid; octahydroindole-2-carboxylic acid; decahydroquinoline-2-carboxylic acid; octahydrocyclopenta[b]pyrrole-2-carboxylic acid; 2-azabicyclo[2.2.2]octane-3-carboxylic acid; 2-azabicyclo[2.2.1]heptane-3-carboxylic acid; 2-azabicyclo[3.1.0]hexane-3-carboxylic acid; 2-azaspiro[4.4]nonane-3-carboxylic acid; 2-azaspiro[4.5]-decane-3-carboxylic acid; spiro[(bicyclo[2.2.1]-heptane)-2,3-pyrrolidine-5-carboxylic acid; spiro[(bicyclo[2.2.2]octane)-2,3-pyrrolidine-5-carboxylic acid; 2-azatricyclo[4.3.0.1$^{6,9}$]-decane-3-carboxylic acid; decahydrocyclohepta[b]pyrrole-2-carboxylic acid; decahydrocycloocta[b]pyrrole-2-carboxylic acid; octahydrocyclopenta[c]pyrrole; octahydroisoindole-1-carboxylic acid, 2,3,3a,4,6a-hexahydrocyclopenta[b]pyrrole-2-carboxylic acid; 2,3,3a,4,5,7a-hexahydroindole-2-carboxylic acid; tetrahydrothiazole-4-carboxylic acid; isoxazolidine-3-carboxylic acid; pyrazolidine-3-carboxylic acid; hydroxyproline-2-carboxylic acid; all of which can optionally be substituted:

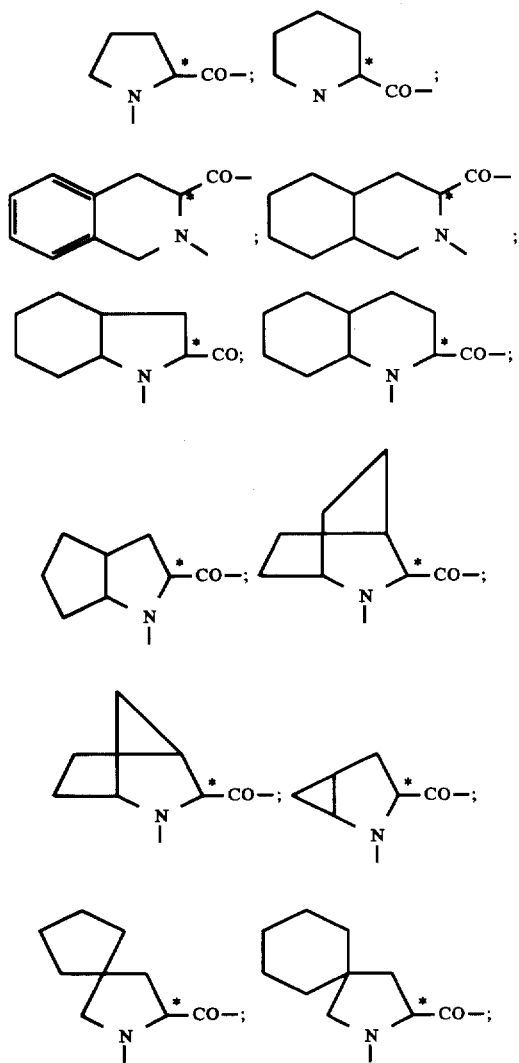
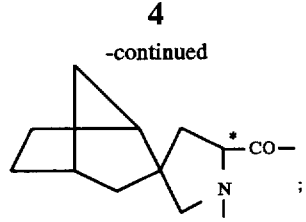
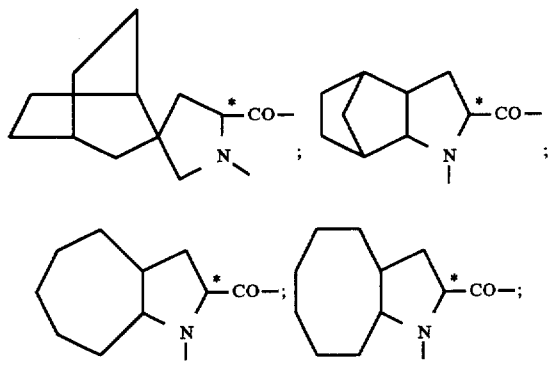
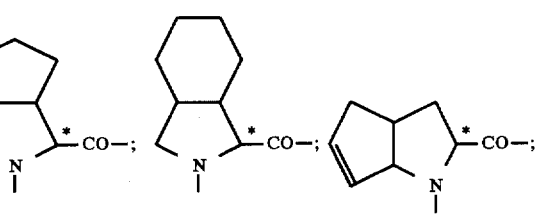
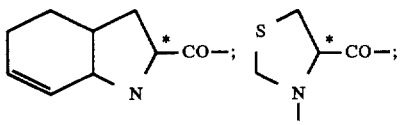
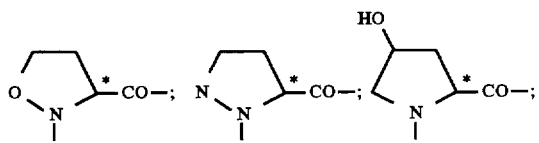

The heterocycles forming the basis of the abovementioned radicals are disclosed, for example, in U.S. Pat. Nos. 4,344,949, 4,374,847, 4,350,704, EP-A 50 800, EP-A 31 741, EP-A 51 020, EP-A 49 658, EP-A 49 605, EP-A 29 488, EP-A 46 953, EP-A 52 870, EP-A 271 865, DE-A 32 26 768, DE-A 31 51 690, DE-A 32 10 496, DE-A 32 11 397, DE-A 32 11 676, DE-A 32 27 055, DE-A 32 42 151, DE-A 32 46 503 and DE-A 32 46 757.

Some of these heterocycles are also proposed in DE-A 38 18 850.3.

Units which can be contained in dipeptides are natural or unnatural amino acids, imino acids and azaamino acids. It is furthermore possible for the natural or unnatural amino acids, imino acids, azaamino acids and dipeptides to be in the form of esters or amides, such as, for example, methyl ester, ethylamide, semicarbazide and ω-amino-$C_4$-$C_8$-alkylamide.

Functional groups of the amino acids, imino acids and dipeptides can be in protected form. Suitable protective groups such as, for example, urethane protective groups, carboxyl protective groups and side-chain protective groups are described in Hubbuch, Kontakte (Merck) 1979, no. 3, pages 14 to 23 and in Büllesbach, Kontakte (Merck) 1980, no. 1, pages 23 to 35. The following may be particularly mentioned:

Aloc, Pyoc, Fmoc, Tcboc, Z, Boc, Ddz, Bpoc, Adoc, Msc, Moc, Z(NO$_2$), Z(Hal$_n$), Bobz, Iboc, Adpoc, Mboc, Acm, tert.-butyl, OBzl, ONbzl, OMbzl, Bzl, Mob, Pic, Trt.

Salts of compounds of the formula (I) mean, in particular, pharmaceutically utilizable or non-toxic salts.

Salts of this type are formed, for example, by compounds of the formula (I) which contain acid groups, for example carboxyl, with alkali metals or alkaline earth metals such as, for example, Na, K, Mg and Ca, and with physiologically tolerated organic amines such as, for example, triethylamine and tris(2-hydroxyethyl)amine.

Compounds of the formula (I) which contain basic groups, for example an amino group or a guanidino group, form salts with inorganic acids such as, for example, hydrochloric acid, sulfuric acid or phosphoric acid and with organic carboxylic or sulfonic acids such as, for example, acetic acid, citric acid, benzoic acid, maleic acid, fumaric acid, tartaric acid and p-toluenesulfonic acid.

Preferred compounds of the formula I are those in which $R^2$ is hydrogen or $C_1$–$C_8$-alkyl which is optionally substituted 1 to 4 times by identical or different radicals from the series comprising hydroxyl, $C_1$–$C_6$-alkoxy, amino, carboxyl, carbamoyl, guanidino, $C_3$–$C_6$-cycloalkyl, halogen and a radical $R^3$, where $R^3$ is $C_6$–$C_{12}$-aryl, $C_6$–$C_{12}$-aryl-$C_1$–$C_4$-alkyl or a mono- or bicyclic 5- to 12-membered heterocyclic aromatic ring which contains as hetero element one or two nitrogen atoms, where, independently of one another, the aryl and heterocyclic radical are optionally substituted once, twice or three times by identical or different radicals from the series comprising $C_1$–$C_6$-alkyl, $C_1$–$C_6$-alkoxy, halogen, nitro, hydroxyl and trifluoromethyl; or is a radical $R^4$, where $R^4$ is $NR^5R^6$; $OR^5$; an amino-acid side-chain; a residue of a natural or unnatural amino acid, imino acid, optionally N—$C_1$–$C_8$-alkylated or $C_6$–$C_{14}$-aryl-$C_1$–$C_8$-alkylated azaamino acid or a dipeptide, and the esters and amides thereof, where free functional groups can optionally be replaced by hydrogen or hydroxymethyl or protected by protective groups customary in peptide chemistry; or is a radical $COR^{4'}$ in which $R^{4'}$ is defined as $R^4$;

$R^5$ and $R^6$ are, independently of one another, hydrogen, $C_1$–$C_8$-alkyl or $C_6$–$C_{12}$-aryl.

Particular mention may be made of compounds of the formula I in which $R^1$ is a radical of the formula II in which R' and R" are, independently of one another, hydrogen or $C_1$–$C_2$-alkyl;

$R^2$ is hydrogen or $C_1$–$C_6$-alkyl which is substituted twice by identical or different radicals $R^4$, where $R^4$ is hydroxyl; amino; an amino-acid side-chain; a residue of a natural or unnatural amino acid, imino acid, optionally N—$C_1$–$C_6$-alkylated or $C_6$–$C_{14}$-aryl-$C_1$—$C_8$-alkylated azaamino acid or a dipeptide in which the peptide linkage can be reduced to NH—CH$_2$, and the esters and amides thereof, where free functional groups can optionally be replaced by hydrogen or hydroxymethyl or protected by protective groups customary in peptide chemistry; or is a radical $COR^{4'}$ in which $R^{4'}$ is defined as $R^4$, or compounds of the formula I in which $R^2$ is methyl which is substituted twice by different radicals $R^4$ and $COR^{4'}$ where $R^4$ and $R^{4'}$ are defined as described above.

Very particularly preferred compounds of the formula I are those in which $R^1$ is a radical of the formula II in which R' and R" are hydrogen, $R^2$ is hydrogen or $C_1$–$C_6$-alkyl which is substituted once or twice, independently of one another, by —OH, NH$_2$, —COOH, —CONH$_2$, —NH—C(NH$_2$)=NH, $C_5$–$C_8$-cycloalkyl, a radical $R^3$ where $R^3$ is $C_6$–$C_{14}$-aryl which can optionally be substituted by hydroxyl, is a bicyclic 8- to 12-membered heterocyclic aromatic ring which contains as hetero element a nitrogen atom, or a radical $R^4$ where $R^4$ is $NR^5R^6$, a residue of a natural or unnatural amino acid, imino acid, optionally N—$C_1$–$C_4$-alkylated or N—$C_6$–$C_{14}$-aryl-$C_1$–$C_4$-alkylated azaamino acid or a dipeptide, and the amides thereof, or a radical $COR^{4'}$ in which $R^{4'}$ is defined as $R^4$, $R^5$ is hydrogen, $R^6$ is $C_1$–$C_6$-alkyl, and n is 3.

Hydantoins are very generally produced by basic treatment of alkoxycarbonyl- or aralkoxycarbonyl-peptides of the formula III [J. S. Fruton and M. Bergmann, J. Biol. Chem. 145 (1942) 253–265; C. A. Dekker, S. P. Taylor, Jr. and J. S. Fruton, J. Biol. Chem. 180 (1949) 155–173; M. E. Cox, H. G. Garg, J. Hollowood, J. M. Hugo, P. M. Scopes and G. T. Young, J. Chem. Soc. (1965) 6806–6813; W. Voelter and A. Altenburg, Liebigs Ann. Chem. (1983) 1641–1655]:

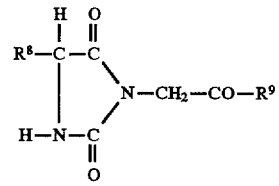

in which $R^7$ is benzyl or tert.-butyl, $R^8$ is any desired amino-acid side-chain and $R^9$ is an amide, a residue of an amino acid or of a peptide. However, the N-terminal amino acid racemizes in this case [W. Voelter and A. Altenburg, Liebigs Ann. Chem. (1983) 1641–1655].

A mild method by contrast is the cyclization to the hydantoins from compounds of the formula III under neutral conditions by treatment with tetrabutylammonium fluoride in refluxing tetrahydrofuran [J. Pless, J. Org. Chem. 39 (1974) 2644–2646].

Another possibility for mild cyclization is the trimethylsilylation of the peptide linkage between the N-terminal amino acid and the adjacent glycine with bistrimethylsilyl-trifluoroacetamide in acetonitrile (4 hours under reflux) [J. S. Davies, R. K. Merritt and R. C. Treadgold, J. Chem. Soc. Perkin Trans. I (1982) 2939–2947].

It has now been found, surprisingly, that peptides of the formula IIIa cyclize to the hydantoin derivatives even at room temperature after a lengthy period or on briefly refluxing with tetrahydrofuran.

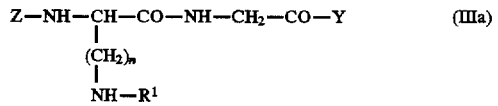

where

Z is benzyloxycarbonyl and

Y is OtBu, Asp(OtBu)-NH—$R^2$ where possible carboxyl groups ought to be in the ester form, and n, $R^1$ and $R^2$ are defined as described above.

Condensation of nitroarginine or nitrohomoarginine with ethyl isocyanatoacetate results in urea derivatives which cyclize to hydantoin derivatives of the formula VIa by heating in hydrochloric acid, with hydrolysis of the ester (K. Schögl and H. Fabitschowitz, Monatsh. Chem. 84 (1953), 937):

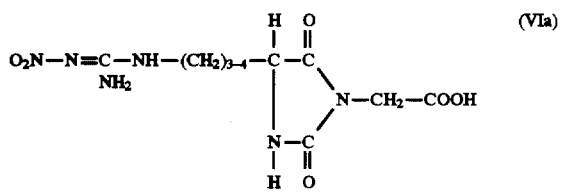

Thus the invention also relates to the preparation of the compounds of the formula I, which comprises $a_1$) heating compounds of the formula IV

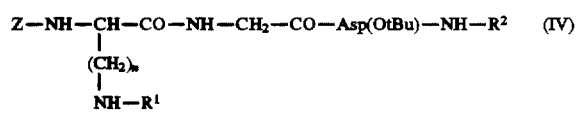

in which Z, $R^1$, $R^2$ and n have the meanings described above, in tetrahydrofuran under reflux for about 2-3 hours, or $a_2$) condensing compounds of the formula VI and VII

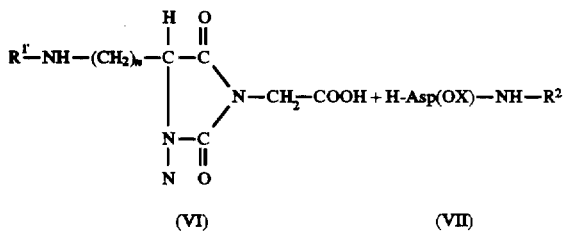

in which $R^{1'}$ is —$C(NH_2)=N—NO_2$ or is defined as $R^1$ above,

X is tBu or Bzl, and $R^2$ and n have the meanings described above, by general methods of peptide chemistry, and b) converting the hydantoins of the general formula V which have been produced in this way

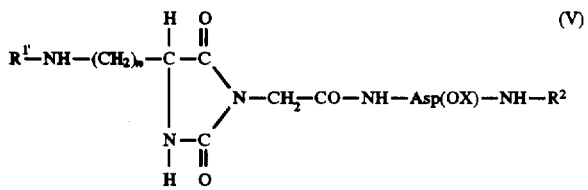

by catalytic hydrogenation and/or acid elimination of the protective groups into the compounds of the formula I according to the invention.

The compounds of the formula VI are novel. They are obtained from the compounds of the formula IIIa, (Y=OtBu) by heating in tetrahydrofuran and subsequent treatment with trifluoroacetic acid or as described for the preparation of the compounds of the formula VIa.

The initial peptides of the formula IV and VII are usually synthesized stepwise starting from the C-terminal end. The peptide linkages can be carried out using the coupling methods known from the literature of peptide chemistry (for example Houben-Weyl, Methoden der organischen Chemie, volume 15/2; B. Merrifield J. Am. Chem. Soc. 85 (1963) 2149; R. Sheppard, Int. J. Peptide Protein res. 21 (1983) 118).

The compounds of the formula I according to the invention have the ability to inhibit the cell-cell adhesion which is based on an interaction of Arg-Gly-Asp-containing glycoproteins with the so-called integrins. Integrins are transmembrane glycoproteins, receptors for Arg-Gly-Asp-containing-cell matrix glycoproteins [E. Ruoslahti and M. D. Pierschbacher, Science 238 (1987) 491–497; D. R. Phillips, I. F. Charo, L. V. Parise and L. A. Fitzgerald, Blood 71 (1988) 831–843].

The novel hydantoin derivatives of the formula I according to the invention inhibit platelet aggregation, metastasis and binding of osteoclasts to bone surfaces.

Thus an acute use of hydantoin derivatives of the formula I is where there is a risk of thrombosis and the risk of reocclusion in cases of myocardial infarct; a chronic use is for the prevention of arteriosclerosis. Another use is during cancer surgery and for the prophylaxis of cancer. In addition, osteoporosis can be averted by inhibiting binding of osteoclasts to bone surfaces.

Thus, the invention also relates to a method of inhibiting platelet aggregation by administering an effective amount of a compound of the formula I or a pharmaceutically acceptable salt thereof, to a method of inhibiting the binding of osteoclasts to the surface of bone by administering an effective amount of a compound of the formula I or a pharmaceutically acceptable salt thereof, and to a pharmaceutical composition containing a compound of the formula I or the physiologically tolerated salt thereof and a physiologically acceptable vehicle.

Advantages of the hydantoin compounds according to the invention compared with hitherto known Arg-Gly-Asp-containing peptides [M. D. Pirschbacher and E. Ruoslahti, Nature 309 (1984) 30–33; M. D. Pirsckbacher and E. Ruoslahti, J. Biol. Chem. 262 (1987) 17294–17298; H. M. Charon et al., Amer. Peptide Symp. 1989; F. E. -F. Ali et al., Amer. Peptide Symp. 1989, p. 94–99; EP-A2 341 915] are, besides the high potency, especially .the greater enzymatic stability and the longer half-life.

The compounds are particularly tested for their inhibitory action on the aggregation of blood platelets and the adhesion of fibrinogen to blood platelets. Gel-filtered blood platelets from donated human blood are used and are activated with ADP or thrombin.

Inhibition of platelet aggregation to human GFP (gel-filtered platelets) stimulated with adenosine diphosphate (ADP) or thrombin (THR) (Marguerie, Plow and Edgington, J. Biol. Chem. 254 (1979) 5357–5363)

| | IC₅₀ (μM) | |
|---|---|---|
| | ADP | THR |
| Z—D—Arg—Gly—Asp—NH—Mbh | 20 | 20 |
| H—D—Arg—Gly—Asp—NH—Mbh | 50 | 30 |
| CO—D—Arg—Gly—Asp—NH—Mbh (cyclic) | 4 | 3 |
| Z—D—Arg—Gly—Asp—NH₂ | 100 | 80 |
| H—D—Arg—Gly—Asp—NH₂ | 500 | 100 |
| CO—D—Arg—Gly—Asp—NH₂ (cyclic) | 20 | 15 |
| H—Arg—Gly—Asp—NH—Mbh | 100 | 80 |
| CO—Arg—Gly—Asp—NH—Mbh (cyclic) | 10 | 4 |
| H—Arg—Gly—Asp—NH₂ | 500 | 200 |
| CO—Arg—Gly—Asp—NH₂ (cyclic) | 40 | 40 |
| CO—Arg—Gly—Asp—Phe—OH (cyclic) | 10 | 3 |
| CO—Arg—Gly—Asp—Arg—Trp—NH₂ (cyclic) | 10 | 7 |
| CO—Arg—Gly—Asp—Val—OH (cyclic) | 1 | 0.5 |
| CO—Arg—Gly—Asp—Val—NH₂ (cyclic) | 10 | 3 |
| CO—Arg—Gly—Asp—Arg—Val—NH₂ (cyclic) | 9 | 4.5 |
| CO—Arg—Gly—Asp—Arg-isobutylamide (cyclic) | 5.5 | 2.5 |
| CO—Arg—Gly—Asp—Phe—Azagly—NH₂ (cyclic) | 30 | 10 |
| CO—Arg—Gly—Asp—Phe—N(CH₃)—NH—CONH₂ (cyclic) | 60 | 20 |
| CO—Arg—Gly—Asp—Phe—N(2-naphthylmethyl)-NH—CONH₂ (cyclic) | 15 | 7 |
| CO—Arg—Gly—Asp—Gln—OH (cyclic) | 3 | 1.5 |
| CO—Arg—Gly—Asp—Arg-4-Abu—OH (cyclic) | 15 | 4 |
| CO—Arg—Gly—Asp—Ser—OH (cyclic) | 10 | 4 |
| CO—Arg—Gly—Asp—Arg—Hyp—NH—C₂H₅ (cyclic) | 3 | 4 |

CO—Arg—Gly— = 5-(S)-(3-Guanidino-propyl)-2,4-dioxo-imidazolidin-3-yl)-acetyl-
Mbh = 4,4'-Dimethoxybenzhydryl Abbreviations:

| | |
|---|---|
| Acm | acetamidomethyl |
| Adoc | 1-adamantyloxycarbonyl |
| Adpoc | 1-(1-adamantyl)-1-methylethoxycarbonyl |
| Aloc | allyloxycarbonyl |
| Boc | tert.-butyloxycarbonyl |
| Bpoc | 1-(4-biphenylyl)-1-methylethoxycarbonyl |
| Cha | cyclohexylalanine |

| | |
|---|---|
| Chg | cyclohexylglycine |
| DCC | dicyclohexylcarbodiimide |
| Ddz | α,α-dimethyl-3,5-dimethoxybenzyloxycarbonyl |
| Dobz | 4-dihydroxyborylbenzyloxycarbonyl |
| Fmoc | 9-fluorenylmethyloxycarbonyl |
| HOBt | 1-hydroxybenzotriazole |
| HOObt | 3-hydroxy-4-oxo-3,4-dihydro-1,2,3-benzotriazine |
| Iboc | isobornyloxycarbonyl |
| Mboc | 1-methylcyclobutyloxycarbonyl |
| Moc | 4-methoxybenzyloxycarbonyl |
| Msc | methylsulfonylethyloxycarbonyl |
| Npg | neopentylglycine |
| Pyoc | 4-pyridylmethyloxycarbonyl |
| Tbg | tert.-butylglycine |
| Tcboc | 2,2,2-trichloro-tert.-butyloxycarbonyl |
| Thia | 2-thienylalanine |
| Z | benzyloxycarbonyl |
| Z(Hal$_n$) | halogen-substituted benzyloxycarbonyl |
| Z(NO$_2$) | 4-nitrobenzyloxycarbonyl |

EXAMPLES

Amino-acid analysis: Hydrolysis in 6N HCl (120° C. for 24 hours). The content of Arg and Gly is greatly reduced in the hydantoin derivatives (B. Schwenzer, E. Weber and G. Losse, J. Prakt. Chem. 327 (1985) 479–486).

1. [5-(3-Guanidino-propyl)-2,4-dioxo-imidazolidin-3-yl] acetyl-L-aspartic acid 4,4'-dimethoxybenzhydrylamide and [5-(3-guanidino-propyl)-2,4-dioxoimidazolidin-3-yl]acetyl-L-aspartamide.

1a. Z-Asp(OtBu) 4,4'-dimethoxybenzhydrylamide 2.6 ml of N-ethylmorpholine and 4.4 g of dicyclohexylcarbodiimide (DCC) were added at 0° C. to a solution of 6.5 g (20 mmol) of Z-Asp(OtBu)-OH, 5.6 g (20 mmol) of 4,4'-dimethoxybenzhydrylamine hydrochloride and 2.7 g of 1-hydroxybenzotriazole (HOBt) in 30 ml of dimethylacetamide. The mixture was stirred at 0° C. for 1 h and then left to stand at room temperature overnight. The precipitate was filtered off with suction, and the filtrate was concentrated. The residue was partitioned between water and ethyl acetate. The organic phase was washed successively with saturated NaHCO$_3$ solution, KHSO$_4$/K$_2$SO$_4$ buffer, saturated NaHCO$_3$ solution and water and then dried over Na$_2$SO$_4$ and concentrated. The residue was. triturated with petroleum ether, filtered off with suction and dried in vacuo.

Yield 10 g.

For further purification, the substance was dissolved in 35 ml of hot isopropanol, and petroleum ether was added. The mixture was left to cool, filtered with suction and dried in vacuo.

Yield 8.7 g; Melting point 126°–127°, $[\alpha]_D^{20}=-1.0°$ (c=1 in dimethylformamide).

1b. H-Asp(OtBu) 4,4'-dimethoxybenzhydrylamide hydrochloride 8.5 g (15.5 mmol) of Z-Asp(OtBu) 4,4'-dimethoxybenzhydrylamide were suspended in 400 ml of methanol and hydrogenated catalytically (Pd on BASO$_4$) at pH 4.5 with the addition of methanolic hydrochloric acid using an autoburet. After the hydrogenation was complete, the catalyst was filtered off with suction, and the filtrate was concentrated. The residue was triturated with petroleum ether, filtered off with suction and dried.

Yield 6.89 g.

A small sample (980 mg) was dissolved in 100 ml of water for purification. Insolubles were filtered off, and the clear solution was freeze-dried.

Yield 950 mg; $[\alpha]_D^{20}=+2.2°$ (c=1 in water).

1c. Z-Gly-Asp(OtBu) 4,4'-dimethoxybenzhydrylamide 3.3 g of Z-Gly-OObt were added to a solution of 4.2 g (9.3 mmol) of unpurified H-Asp (OtBu) 4,4'-dimethoxybenzhydrylamide hydrochloride and 1.21 ml of N-ethylmorpholine in 50 ml of dimethylformamide, and the mixture was stirred until everything had dissolved and was left to stand at room temperature overnight. The solution was concentrated in vacuo, and the residue was worked up as described in Experiment 1a.

Yield 4.83 g (85.5%); $[\alpha]_D^{21}=-13.7°$ (c=1 in methanol)

1d. H-Gly-Asp(OtBu) 4,4'-dimethoxybenzhydrylamide hydrochloride 4.7 g (7.75 mmol) of Z-Gly-Asp(OtBu) 4,4'-dimethoxybenzhydrylamide were hydrogenated catalytically as described in Example 1b. The residue was triturated with ether.

Yield 3.84 g.

A small sample (800 mg) was purified as described in Example 1b.

Yield 779 mg; $[\alpha]_D^{21}=-24.8°$ (c=1 in water).

1e. Z-D-Arg-Gly-Asp (OtBu) 4,4'-dimethoxybenzhydrylamide 0.66 g of DCC was added at 0° C. to a solution of 0.93 g (3 mmol) of Z-D-Arg-0H, 1.52 g (3 mmol) of H-Gly-Asp(OtBu) 4,4'-dimethoxybenzhydrylamide hydrochloride and 0.41 g of HOBt in 10 ml of dimethylformamide. The mixture was left to stir at 0° C. for 1 hour and then to stand at room temperature overnight. The recipitate was filtered off with suction, and the filtrate was concentrated. The residue was partitioned between n-pentanol and 50% saturated NaHCO$_3$ solution. The organic phase was extracted by shaking 3 more times with NaHCO$_3$ solution and once with water, and was concentrated. The residue was triturated with petroleumether, filtered off with suction and dried.

Yield 1.45 g. The substance was used without purification for the next stage.

1f. [5-(R)-(3-guanidino-propyl)-2,4-dioxo-imidazolin-3-yl]acetyl Asp 4,4'-dimethoxybenzhydrylamide and [5-(R)-(3-guanidino-propyl)-2,4-dioxo-imidazolidin-3-yl]acetyl-L-Asp-amide 15.5 g of Z-D-Arg-Gly-Asp(OtBu)-NH-Mbh are refluxed in 775 ml of absolute tetrahydrofuran for 2 hours. The mixture is then concentrated and the residue is dried under high vacuum. Yield 14.6 g. The residue obtained above is dissolved in 75 ml of methylene chloride. 75 ml of trifluoroacetic acid are added to the mixture which is then left to stand at room temperature for 30 minutes. It is concentrated. The residue is triturated with ether, filtered off with suction and dried.

Yield 12.2 g.

6.1 g of the crude substance obtained above are chromatographed on ®Sephadex LH 20 (column: 4×200cm; eluent: 0.5M acetic acid/methanol 7.5:6).

Fraction X. 5-XIII. 6: 540 mg. Mass spectrum (M+1 peak at 372 ) and amino-acid analysis (Asp 1.00, Gly 0.40, Arg 0.35; peptide content 86.5% ) indicate that this fraction is [5-(3-guanidinopropyl)-2,4-dioxo-imidazolidin-3-yl]acetyl-Asp-NH$_2$.

Fraction XIX.5-XXIII.6:2.86 g. Mass spectrum (M+1 peak at 598) and amino-acid analysis (Asp 0.99, Gly 0.38, Arg 0.34; peptide content 88%) indicate that this fraction is 5-(3-guanidinopropyl)-2,4-dioxo-imidazolidin-3-yl]acetyl-Asp 4,4'-dimethoxybenzhydrylamide.

Example 2

[5-(S)-(3-guanidino-propyl)-2,4-dioxo-imidazolidin-3-yl] acetyl-Asp 4,4'-dimethoxybenzhydrylamide and [5-(S)-(3-guanidinopropyl)-2,4-dioxo-imidazolidin-3-yl]acetyl-Asp-amide 2a. Z-Arg-Gly-Asp(OtBu) 4,4'-dimethoxybenzhydrylamide Reaction and working up are carried out in analogy to Example 1e on 1.54 g of Z-Arg-OH and 2.54 g of HCl.H-Gly-Asp(OtBu)—NH—Mbh with 675 mg of HOBt and 1.1 g of DCC in 25 ml of dimethylformamide. Yield 4.2 g of crude substance, $[\alpha]^{21}=-18°$ (c=1 in methanol).

2b. [5-(S)-(3-Guanidino-propyl)-2,4-dioxo-imidazolidin-3-yl]acetyl-Asp 4,4'-dimethoxybenzhydrylamide and [5-(S)-(3-guanidinopropyl)-2,4-dioxo-imidazolidin-3-yl]acetyl-Asp-amide In analogy to Example 1f, 3.65 g of Z-Arg-Gly-Asp (OtBu) 4,4'-dimethoxybenzhydrylamide in 170 ml of absolute tetrahydrofuran are heated under reflux and then the protective groups are eliminated in methylene chloride/ trifluoroacetic acid. Yield 3.15 g. The substance obtained in this way is purified as described in Example 1f:

Fraction III.3–IV.7:485 mg. Mass spectrum (M+1 peak at 372) and amino-acid analysis (Asp 0.99, Gly 0.36, Arg 0.37; peptide content: 60%) indicate that this fraction is [5-(S)-(3-guanidinopropyl)-2,4-dioxo-imidazolidin-3-yl]acetyl-Asp-amide.

Fraction VI.7–VII.7:1.54 g. Mass spectrum (M+1 peak at 598) and amino-acid analysis (Asp 0.99, Gly 0.36, Arg 0.3; peptide content: 78%) indicate that this fraction is [5-(S)-(3-guanidinopropyl)-2,4-dioxo-imidazolidin-3-yl]acetyl-Asp 4,4'-dimethoxybenzhydrylamide.

Example 3

[5-(S)-(3-Guanidino-propyl)-2,4-dioxo-imidazolidin-3-yl] acetyl-Asp-Phe-OH

3a. Z-Arg-Gly-OtBu 39.6 g of DCC are added at 0° C. to a solution of 55 g of Z-Arg-OH, 30.18 g of HCl.H-Gly-OtBu and 24.3 g of HOBt in 400 ml of dimethylformamide. The mixture is left to stir at 0° C. for 1 hour and at room temperature for 3 hours and to stand at room temperature overnight. The DC-urea is filtered off with suction and the filtrate is concentrated. The residue is subjected to countercurrent partition between ethyl acetate and saturated NaHCO$_3$ solution (400 ml each). This results in the required substance precipitating in the first separating funnel after the 3rd stage.

Yield 40.2 g.

The mother liquor and the other ethyl acetate phases were concentrated together and once again subjected to countercurrent partition. between ethyl acetate and NaHCO$_3$. Once again, the required substance precipitated in the first separating funnel after the 3rd stage.

Yield 27.8 g. Total yield: 68 g (89.6%), melting point 112°–116° C. with decomposition.

3b. [5-(S)-(3-Guanidino-propyl)-2,4-dioxo-imidazolidin-3-yl]acetic acid 67.5 g of Z-Arg-Gly-OtBu are suspended in 800 ml of absolute tetrahydrofuran and refluxed for 2 hours. The mixture is then concentrated and the residue is triturated with methyl tert.-butyl ether. The precipitate is filtered off with suction and dried. Yield 54.2 g.

53.5 g of the substance obtained above are dissolved in 535 ml of 90% strength aqueous trifluoroacetic acid. The mixture is left to stand at room temperature for 1 hour and is concentrated. The residue is triturated with diethyl ether, filtered off with suction and dried. Yield 53 g of [5-(S)-(3-guanidino-propyl)-2,4-dioxo-imidazolidin-3-yl]acetic acid trifluoroacetate.

To remove the trifluoroacetic acid, the substance obtained above is chromatographed on 800 ml of weakly basic ion exchanger (IRA-93) in water at 50° C. Most of the substance precipitates as crystals out of the eluate on cooling. Yield 24.9 g, melting point 287°–292° C.; $[\alpha]_D^{21}=1.0°$ (c=1 in glacial acetic acid).

3c. [5-(S)-(3-Guanidino-propyl)-2,4-dioxo-imidazolidin-3-yl]acetyl-Asp(OtBu)-Phe-OtBu 0.66 g of DCC is added at 0° C. to a solution of 1.29 g of HCl.H-Asp(OtBu)-Phe-OtBu, 0.772 g of [5-(S)-(3-guanidinopropyl)-2,4-dioxo-imidazolidin-3-yl]acetic acid and 0.41 g of HOBt in 30 ml of dimethylformamide, and the mixture is left to stir at 0° C. for 1 hour and to stand at room temperature overnight. The precipitate is filtered off with suction and the filtrate is concentrated. The residue is triturated with diethyl ether, and the residue is chromatographed on ®Sephadex LH$_{20}$ (column 4×200 cm; eluent: glacial acetic acid/n-butanol/water 3.5:4.3:43).

Yield 800 mg, $[\alpha]_D^{22}=-25.1°$ (c=1 in methanol)

3d. [5-(S)-(3-guanidino-propyl)-2,4-dioxo-imidazolidin-3-yl]acetyl-Asp-Phe-OH 610 mg of [5-(R)-(3-guanidino-propyl)-2,4-dioxoimidazolidin-3-yl]acetyl-Asp(OtBu)-Phe-OtBu are dissolved in 5 ml of 90% strength aqueous trifluoroacetic acid. The mixture is left to stand at room temperature for 1 hour and is concentrated. The residue is extracted by shaking with water and diethyl ether and is freeze-dried.

Yield 490 mg, $[\alpha]_D^{23}=-18.2°$ (c=1 in water).

Example 4

[5-(S)-(3-Guanidino-propyl)-2,4-dioxo-imidazolidin-3-yl] acetyl-Asp-Arg-Trp-NH$_2$ In analogy to Example 3c, 0.772 g of [5-(S)-(3-guanidinopropyl)-2,4-dioxo-imidazolidin-3-yl]acetic acid and 2.625 g of H-Asp(OtBu)-Arg-Trp-NH$_2$ ditosylate are reacted with 0.41 g of HOBt and 0.68 g of DCC in 30 ml of dimethylformamide and purified. Yield 1.8 g.

160 mg of the above compound are dissolved in 3 ml of a 9:1 mixture of 90% strength aqueous trifluoroacetic acid/ dimercaptoethane. The mixture is left to stand at room temperature for 1 hour and concentrated, the residue is dissolved in water and extracted by shaking 3 times with diethyl ether. The aqueous phase is filtered and freeze-dried. Yield 140 mg, $[\alpha]_D^{21}=-25.2°$ (c=1 in water).

Example 5

[5-(S)-(3-Guanidino-propyl)-2,4-dioxo-imidazolidin-3-yl] acetyl-Asp-Val-OH

In analogy to Example 3c, 438 mg of [5-(R)-(3-Guanidino-propyl)-2,4-dioxo-imidazolidin-3-yl]acetic acid and 648 mg of HCl.H-Asp(OtBu)-Val-OtBu are reacted with 230 mg of HOBt and 374 mg of DCC in 20 ml of dimethylformamide and purified: Yield 892 mg.

The above substance is reacted in 9 ml of 90% strength trifluoroacetic acid in analogy to Example 3d.

Yield 767 mg, $[\alpha]_D^{21}=-36.6'$(c=1 in water).

Example 6

[5-(S)-(3-Guanidino-propyl)-2,4-dioxo-imidazolidin-3-yl] acetyl-Asp-Val-NH$_2$

In analogy to Example 3c, 772 g of [5-(S)-(3-Guanidino-propyl)-2,4-dioxo-imidazolidin-3-yl]acetic acid and 971 mg of HCl.H-Asp(OtBu)-Val-NH$_2$ are reacted with 410 mg of HOBt and 680 mg of DCC in 30 ml of dimethylformamide and purified.

Yield 950 mg, $[\alpha]_D^{21}=-41.2'$(c=1 in water).

The substance obtained above is reacted in 10 ml of 90% strength trifluoroacetic acid in analogy to Example 3d.

Yield 780 mg, $[\alpha]_D^{21}=-43.1°$ (c=1 in water).

Example 7

[5-(S)-(3-Guanidino-propyl)-2,4-dioxo-imidazolidin-3-yl] acetyl-Asp-Arg-Val-NH$_2$ acetate In analogy to Example 3c, 515 mg of [5-(R)-(3-guanidino-propyl)-2,4-dioxo-imidazolidin-3-yl]acetic acid and 1.58 g of H-Asp(OtBu)-Arg-Val-NH$_2$ ditosylate are reacted with 270 mg of HOBt and 440 mg of DCC in 20 ml of dimethylformamide and purified. Yield 950 mg.

430 mg of the substance obtained above are reacted in 5 ml of 90% strength trifluoroacetic acid in analogy to Example 3d.

Yield 380 mg, $[\alpha]_D^{20}=-23.2°$ (c=1 in water)

Example 8

[5-(S)-(3-Guanidino-propyl)-2,4-dioxo-imidazolidin-3-yl] acetyl-Asp-Arg isobutylamide acetate In analogy to Example 3c, 515 mg of [5-(S)-(3-guanidino-propyl)-2,4-dioxo-imidazolidin-3-yl]acetic acid and 1.49 g of H-Asp(OtBu)-Arg isobutylamide ditosylate are reacted with 270 mg of HOBt and 440 mg of DCC in 20 ml of dimethylformamide and purified. Yield 1.2 g.

360 mg of the substance obtained above are reacted in 5 ml of 90% strength trifluoroacetic acid in analogy to Example 3d.

Yield 370 mg, $e\alpha]_D^{20}=-28.3°$ (c=1 in water)

Example 9

[5-(S)-(3-Guanidino-propyl)-2,4-dioxo-imidazolidin-3-yl] acetyl-Asp-Gln-OH

In analogy to Example 3c, 770 mg of [5-(S)-(3-guanidino-propyl)-2,4-dioxo-imidazolidin-3-yl]acetic acid and 1.23 g of HCl.H-Asp(OtBu)-Gln-OtBu are reacted with 410 mg of HOBt and 660 mg of DCC in 20 ml of dimethylformamide and purified.

Yield 891 mg.

850 mg of the substance obtained above are reacted in 8 ml of 90% strength trifluoroacetic acid in analogy to Example 3d.

Yield 742 mg, $[\alpha]_D^{21}=-29.5°$ (c=1 in water)

Example 10

[5-(S)-(3-Guanidino-propyl)-2,4-dioxo-imidazolidin-3-yl] acetyl-Asp-Arg-4-Abu-OH acetate In analogy to Example 3c, 515 mg of [5-(S)-(3-guanidino-propyl)-2,4-dioxo-imidazolidin-3-yl]acetic acid and 1.12 g of 2 HCl.H-Asp(OtBu)-Arg-4-Abu-OtBu are reacted with 270 mg of HOBt and 440 mg of DCC in 20 ml of dimethylformamide and purified. Yield 550 mg.

300 mg of the substance obtained above are reacted in 3 ml of 90% strength trifluoroacetic acid in analogy to Example 3d.

Yield 288 mg, $[\alpha]_D^{21}=-29.8°$ (c=1 in water).

Example 11

[5-(S)-(3-Guanidino-propyl)-2,4-dioxo-imidazolidin-3-yl] acetyl-Asp-Ser-OH

In analogy to Example 3c, 770 mg of [5-(S)-(3-guanidino-propyl)-2,4-dioxo-imidazolidin-3-yl]acetic acid and 1.27 g of HCl.H-Asp(OtBu)-Ser(tBu)-OtBu are reacted with 410 mg of HOBt and 660 mg of DCC in 20 ml of dimethylformamide and chromatographed on silica gel (mobile phase: methylene chloride/methanol/glacial acetic acid/water 8:2:0.2:0.2).

700 mg of the substance obtained above are reacted in 7 ml of 90% strength trifluoroacetic acid in analogy to Example 3d.

Yield 579 mg, $[\alpha]_D^{21}=-19.1°$ (c=1 in water).

Example 12

[5-(S)-(3-Guanidino-propyl)-2,4-dioxo-imidazolidin-3-yl] acetyl-Asp-Arg-Hyp-NH—C$_2$H$_5$ acetate In analogy to Example 3c, 515 mg of [5-(S)-(3-guanidino-propyl)-2,4-dioxo-imidazolidin-3-yl]acetic acid and 1.66 g of H-Asp(OtBu)-Arg-Hyp-NHC$_2$H$_5$ ditosylate are reacted with 270 mg of HOBt and 440 mg of DCC in 20 ml of dimethylformamide and purified.

Yield 947 mg.

600 mg of the substance obtained above are reacted in 6 ml of 90% strength trifluoroacetic acid in analogy to Example 3d.

Yield 574 mg, $[\alpha]_D^{21}=-43.7°$ (c=1 in water).

Example 13

[5-(S)-(3-Guanidino-propyl)-2,4-dioxo-imidazolidin-3-yl] acetyl-Asp-Phe-Azagly-NH$_2$ In analogy to Example 3c, 600 mg of [5-(S)-(3-guanidino-propyl)-2,4-dioxo-imidazolidin-3-yl]acetic acid and 1 g of HCl.H-Asp(OtBu)-Phe-Azagly-NH$_2$ are reacted with 327 mg of HOBt and 490 mg of DCC in 15 ml of dimethylformamide and purified.

Yield 800 mg.

540 mg of the substance obtained above are reacted in 10 ml of 90% strength trifluoroacetic acid in analogy to Example 3d.

Yield 500 mg, $[\alpha]_D^{21}=-35°$ (c=1 in glacial acetic acid).

Example 14

[5-(S)-(3-Guanidino-propyl)-2,4-dioxo-imidazolidin-3-yl] acetyl-Asp-Phe-N(CH$_3$)—NH—CO—NH$_2$ In analogy to Example 3c, 257 mg of [5-(S)-(3-guanidino-propyl)-2,4-dioxo-imidazolidin-3-yl]acetic acid and 540 mg of HCl.H-Asp(OtBu)-Phe-N(CH$_3$)—NH—CO—NH$_2$ are reacted with 185 mg of HOBt and 278 mg of DCC in 10 ml of dimethylformamide and purified on silica gel (glacial acetic acid/n-butanol/water 1:8:1).

Yield 670 mg.

460 mg of the substance obtained above are reacted in 20 ml of 90% strength trifluoroacetic acid in analogy to Example 3d.

Yield 400 mg, $[\alpha]_D^{20}=-10°$ (c=1 in glacial acetic acid).

Example 15

[5-(S)-(3-Guanidino-propyl)-2,4-dioxo-imidazolidin-3-yl] acetyl-Asp-Phe-N(2-naphthylmethyl)NH—CO—NH$_2$ In analogy to Example 3c, 169 mg of [5-(S)-(3-guanidino-propyl)-2,4-dioxo-imidazolidin-3-yl]acetic acid and 380 mg of HCl.H-Asp (OtBu)-Phe-N(2-naphthylmethyl)-NH—CO—NH$_2$ are reacted with 93 mg of HOBt and 139 mg of DCC in 10 ml of dimethylformamide and purified on silica gel (methylene chloride/methanol/water/acetic acid 8:2:0.2:0.2).

Yield 100 mg.

The substance obtained above is reacted in 10 ml of 90% strength trifluoroacetic acid in analogy to Example 3d.

Yield 90 mg, $[\alpha]_D^{23}$=−11.2° (c=1 in glacial acetic acid).

Example 16

[5-(S)-(3-Guanidino-propyl)-2,4-dioxo-imidazolidin-3-yl] acetyl-Asp-Phe-N(C$_2$H$_5$)—NH—CO—NH$_2$ In analogy to Example 3c, 365 mg of [5-(R)-(3-guanidino-propyl)-2,4-dioxo-imidazolidin-3-yl]acetic acid and 600 mg of HCl.H-Asp(OtBu)-Phe-N(C$_2$H$_5$)—NH—CO—NH$_2$ are reacted with 199 mg of HOBt and 298 mg of DCC in 5 ml of dimethylformamide and purified on silica gel (n-butanol/water/glacial acetic acid 8:1:1).

Yield 400 mg.

390 mg of the substance obtained above are reacted in 15 ml of 90% strength trifluoroacetic acid in analogy to Example 3d.

Yield 380 mg, $[\alpha]_D^{21}$ =−12.7° (c=1 in glacial acetic acid).

Example 17

[5-(S)-(3-Guanidino-propyl)-2,4-dioxo-imidazolidin-3-yl] acetyl-Asp-Trp-Pro-OH

In analogy to Example 3c, 515 mg of [5-(S)-(3-guanidino-propyl)-2,4-dioxo-imidazolidin-3-yl]acetic acid and 1.154 g of HCl.H-Asp(OtBu)-Trp-Pro-OtBu are reacted with 270 mg of HOBt and 440 mg of DCC in 20 ml of dimethylformamide and purified on silica gel (methylene chloride/methanol/glacial acetic acid/water 8:2:0.15:0.15).

Yield 850 mg.

790 mg of the substance obtained above are reacted in 10 ml of 90% strength trifluoroacetic acid/1,2-ethanedithiol (9:1) in analogy to Example 4.

Yield 750 mg, $[\alpha]_D^{22}$=−45.5° (c=1 in water).

Example 18

[5-(S)-(3-Guanidino-propyl)-2,4-dioxo-imidazolidin-3-yl] acetyl-Asp-Trp-OH

In analogy to Example 3c, 770 mg of [5-(S)-(3-guanidino-propyl)-2,4-dioxo-imidazolidin-3-yl]acetic acid and 1.4 g of HCl.H-Asp(OtBu)-Trp-OtBu are reacted with 410 mg of HOBt and 660 mg of DCC and purified on silica gel (methylene chloride/methanol/glacial acetic acid/water 8:2:0.2:0.2).

Yield 760 mg.

700 mg of the substance obtained above are reacted in 11 ml of 90% strength trifluoroacetic acid/1,2-ethanedithiol (9:1) in analogy to Example 4.

Yield 617 mg, $[\alpha]_D^{21}$=−12.3° (c=1 in water).

Example 19

[5-(S)-(3-Guanidino-propyl)-2,4-dioxo-imidazolidin-3-yl] acetyl-Asp-Trp-Gly-OH

In analogy to Example 3c, 1.21 g of [5-(S)-(3-guanidino-propyl)-2,4-dioxo-imidazolidin-3-yl]acetic acid and 2.47 g of HCl.H-Asp(OtBu)-Trp-Gly-OtBu are reacted with 635 mg of HOBt and 635 mg of DCC in 30 ml of dimethylformamide and purified on silica gel (methylene chloride/methanol/glacial acetic acid/water 9:2:0.2:0.2).

Yield 1 g of oil.

The substance obtained above is reacted in 10 ml of 90% strength trifluoroacetic acid/1,2-ethanedithiol (9:1) in analogy to Example 4.

Yield 0.67 g, $[\alpha]_D^{23}$=−28.2° (c=1 in water).

Example 20

[5-(S)-(3-Guanidino-propyl)-2,4-dioxo-imidazolidin-3-yl] acetyl-Asp-Trp-NH$_2$

From [5-(S)-(3-guanidino-propyl)-2,4-dioxo-imidazolidin-3-yl]acetic acid and HCl.H-Asp(OtBu)-Trp-NH$_2$ in analogy to Example 3c and Example 4.

$[\alpha]_D^{24}$=−19° (c=1 in water)

Example 21

[5-(S)-(3-Guanidino-propyl)-2,4-dioxo-imidazolidin-3-yl] acetyl-Asp-NH—(CH$_2$)$_4$-NH$_2$ acetate From [5-(S)-(3-guanidino-propyl)-2,4-dioxo-imidazolidin-3-yl]acetic acid and HCl.H-Asp(OtBu)-NH—(CH$_2$)$_6$—NH-Boc in analogy to Example 3c and Example 3d.

$[\alpha]_D^{21}$=−22.2° (c=1 in water)

Example 22

[5-(S)-(3-Guanidino-propyl)-2,4-dioxo-imidazolidin-3-yl] acetyl-Asp-L-phenylglycine From [5-(S)-(3-guanidino-propyl)-2,4-dioxo-imidazolidin-3-yl]acetic acid and HCl.H-Asp(OtBu)-Phg-OtBu in analogy to Example 3c and in Example 3d.

$[\alpha]_D^{19}$=+20.7° (c=1 in water)

Example 23

[5-(S)-(3-Guanidino-propyl)-2,4-dioxo-imidazolidin-3-yl] acetyl-Asp-L-hexahydrophenylglycine From [5-(S)-(3-guanidino-propyl)-2,4-dioxo-imidazolidin-3-yl]acetic acid and HCl.H-Asp(OtBu)-L-hexahydrophenyl-glycine-OtBu in analogy to Example 3c and Example 3d.

$[\alpha]_D^{20}$=−30.6 (c=1 in water)

Example 24

[5-(S)-(3-Guanidino-propyl)-2,4-dioxo-imidazolidin-3-yl] acetyl-Asp-L-e-phenylglycinol From [5-(S)-(3-guanidino-propyl)-2,4-dioxo-imidazolidin-3-yl]acetic acid and HCl.H-Asp(OtBu)-L-α-phenylglycinol in analogy to Example 3c and Example 3d.

$[\alpha]_D^{20}$=−9.8° (c=1 in water)

Example 25

[5-(S)-(3-Guanidino-propyl)-2,4-dioxo-imidazolidin-3-yl] acetyl-Asp-D-α-phenylglycinol From [5-(S)-(3-guanidino-propyl)-2,4-dioxo-imidazolidin-3-yl]acetic acid and HCl.H-Asp(OtBu)-D-e-phenylglycinol in analogy to Example 3c and Example 3d.

$[\alpha]_D^{19}$=−49.8° (c=1 in water)

Example 26

[5-(S)-(3-Guanidino-propyl)-2,4-dioxo-imidazolidin-3-yl] acetyl-Asp-Tyr-OH

From [5-(S)-(3-guanidino-propyl)-2,4-dioxo-imidazolidin-3-yl]acetic acid and HCl.H-Asp(OtBu)-Tyr (tBu)-OtBu in analogy to Example 3c and Example 4.

$[\alpha]_D^{17} = -17°$ (c=1 in water)

Example 27

[5-(S)-(3-Guanidino-propyl)-2,4-dioxo-imidazolidin-3-yl]acetyl-Asp-Tyr-NH₂

From [5-(S)-(3-guanidino-propyl)-2,4-dioxo-imidazolidin-3-yl]acetic acid and HCl.H-Asp(OtBu)-Tyr (tBu)-NH₂ in analogy to Example 3c and Example 4.

$[\alpha]_D^{21} = -22.5°$ (c=1 in water)

Example 28

[5-(S)-(3-Guanidino-propyl)-2,4-dioxo-imidazolidin-3-yl]acetyl-Asp-Nal-OH

From [5-(S)-(3-guanidino-propyl)-2,4-dioxo-imidazolidin-3-yl]acetic acid and HCl.H-Asp(OtBu)-Nal-OtBu in analogy to Example 3c and Example 4.

$[\alpha]_D^{21} = -8.7$ (c=1 in water)

Example 29

[5-(S)-(3-Guanidino-propyl)-2,4-dioxo-imidazolidin-3-yl]acetyl-Asp-Nal-Aoc-OH

From [5-(S)-(3-guanidino-propyl)-2,4-dioxo-imidazolidin-3-yl]acetic acid and HCl.H-Asp(OtBu)-Nal-Aoc-OtBu in analogy to Example 3c and Example 4.

$[\alpha]_D^3 = -15.3$ (c=1 in methanol)

Example 30

[5-(S)-(3-Guanidino-propyl)-2,4-dioxo-imidazolidin-3-yl]acetyl-Asp 9-fluorenylamide a) [5-(S)-(3-Nitro-guanidino-propyl)-2,4-dioxo-imidazolidin-3-yl]acetic acid 11 g (0.05 mol) of H-Arg(NO₂)-OH are dissolved with 4.3 g (0.05 mol) of sodium bicarbonate in 200 ml of water under reflux. At 70° C., 7.1 g (0.055 mol) of ethyl isocyanatoacetate are added dropwise. The mixture is stirred at 70° C. for 1 hour, left to cool and stirred at room temperature overnight, 50 ml of concentrated hydrochloric acid are added, the mixture is concentrated, 20 ml of 50% concentrated hydrochloric acid are added, the mixture is heated under reflux for 1 hour and substantially concentrated, and the precipitated product is filtered off with suction.

Melting point 202°–207° C.

b) [5-(S)-(3-Nitro-guanidino-propyl)-2,4-dioxo-imidazolidin-3-yl]acetyl-Asp(OBzl) 9-fluorenylamide 0.15 g (0.5 mmol) of [5-(S)-(3-nitro-guanidino-propyl)-2,4-dioxo-imidazolidin-3-yl]acetic acid is dissolved in 5 ml of dimethylformamide. 0.13 g (0.5 mmol) of disuccinimidyl carbonate and 0.05 g of 4-dimethylaminopyridine are added and then the mixture is stirred at room temperature for 1.5 hours and, after addition of 0.2 ml (2.5 mmol) of N-ethylmorpholine and 0.47 g (0.5 mmol) of H-Asp(OBzl) 9-fluorenylamide trifluoroacetate in 3 ml of dimethylformamide, the mixture is stirred at room temperature overnight. It is evaporated to dryness, methylene chloride is added, and the mixture is extracted with sodium bicarbonate and potassium bisulfate solution. The organic phase is concentrated and the residue is crystallized with methanol/ethyl acetate.

Yield 150 mg, melting point 162°–164° C.

c) [5-(S)-(3-Guanidino-propyl)-2,4-dioxo-imidazolidin-3-yl]acetyl-Asp 9-fluorenylamide 80 mg of [5-(S)-(3-nitro-guanidino-propyl)-2,4-dioxo-imidazolidin-3-yl]acetyl-Asp(OBzl) 9-fluorenylamide are dissolved in 50 ml of dimethylformamide and, after addition of 0.1 g of 10% Pd/C, hydrogenated at 50° C. for 8 hours. Then 50 ml of water are added and hydrogenation is continued at 50° C. for 8 hours. The mixture is filtered hot, the filtrate is concentrated and the residue is stirred with isopropanol and recrystallized from methanol.

Yield 58 mg, melting point >250° C.

We claim:

1. A compound of the formula I

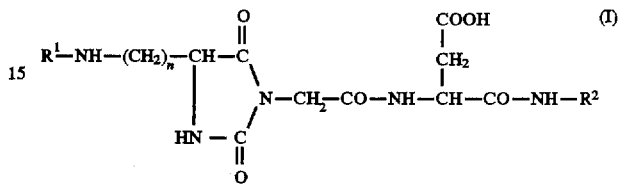

in which n is an integer 3 or 4;

R¹ is C₁–C₆-alkyl or a radical of the formula II

in which

R' and R" are, independently of one another, hydrogen or C₁–C₆-alkyl;

R² is hydrogen, —NH—CO—NH₂ or C₁–C₁₈-alkyl which is optionally substituted one or more times by identical or different radicals from the series comprising hydroxyl, carbamoyl, carboxyl, carboxamido, amino, mercapto, C₁–C₁₈-alkoxy, guanidino, C₃–C₈-cycloalkyl, halogen, nitro, trifluoromethyl and a radical R³, where R³ is C₆–C₁₄-aryl, C₈–C₁₄-aryl-C₁–C₈-alkyl or a mono- or bicyclic 5- to 12-membered heterocyclic ring which can be aromatic, partially hydrogenated or completely hydrogenated and which can contain as hetero element one, two or three identical or different nitrogen, oxygen or sulfur atoms, where the aryl and, independently of one another, the heterocyclic radical is optionally substituted one or more times by identical or different radicals from the series comprising C₁–C₁₈-alkyl, C₁–C₁₈-alkoxy, halogen, hydroxyl, nitro and trifluoromethyl; or is a radical R⁴; where R⁴ is NR⁵R⁶; OR⁵; SR⁵; an amino-acid side-chain; a residue of a natural or unnatural amino acid, imino acid, optionally N—C₁–C₈-alkylated or C₆–C₁₄-aryl-C₁–C₈-alkylated azaamino acid or a dipeptide in which the peptide linkage can be reduced to NH—CH₂, and the esters and amides thereof, where free functional groups can optionally be replaced by hydrogen or hydroxymethyl or protected by the protective groups customary in peptide chemistry; or is a radical COR⁴' in which R⁴' is defined as R⁴;

R⁵ is hydrogen, optionally amino group-substituted C₁–C₁₈-alkyl, C₆–C₁₄-aryl, C₆–C₁₄-aryl-C₁–C₈-alkyl, C₁–C₁₈-alkylcarbonyl, C₁–C₁₈-alkyloxycarbonyl, C₆–C₁₄arylcarbonyl, C₆–C₁₂-aryl-C₁–C₈-alkylcarbonyl, C₆–C₁₈-aryl-C₁–C₁₈-alkyloxycarbonyl, a residue of a natural or unnatural amino acid, imino acid, optionally N—C₁–C₈-alkylated or C₆–C₁₄-aryl-C₁–C₈-alkylated azaamino acid or a dipeptide in which the peptide linkage can be reduced to NH—CH₂;

$R^5$ is hydrogen, $C_1-C_{18}$-alkyl, $C_6-C_{12}$-aryl or $C_6-C_{12}$-aryl-$C_1-C_8$-alkyl;

or a physiologically acceptable salt thereof.

2. A compound of the formula I as claimed in claim 1, wherein $R^2$ is hydrogen or $C_1-C_8$-alkyl which is optionally substituted 1 to 4 times by identical or different radicals from the series comprising hydroxyl, amino, carboxyl, carbamoyl, guanidino, $C_1-C_6$-alkoxy, $C_3-C_6$-cycloalkyl, halogen and a radical $R^3$, where $R^3$ is $C_6-C_{12}$-aryl, $C_6-C_{12}$-aryl-$C_1-C_4$-alkyl or a mono- or bicyclic 5- to 12-membered heterocyclic aromatic ring which contains as hetero element one or two nitrogen atoms, where, independently of one another, the aryl and heterocyclic radical are optionally substituted once, twice or three times by identical or different radicals from the series comprising $C_1-C_6$-alkyl, $C_1-C_6$-alkoxy, halogen, nitro, hydroxyl and trifluoromethyl; or is a radical $R^4$, where $R^4$ is $NR^5R^6$; $OR^5$; an amino-acid side-chain; a residue of a natural or unnatural amino acid, imino acid, optionally $N-C_1-C_8$-alkylated or $C_6-C_{14}$-aryl-$C_1-C_8$-alkylated azaamino acid or a dipeptide, and the esters and amides thereof, where free functional groups can optionally be replaced by hydrogen or hydroxymethyl or protected by protective groups customary in peptide chemistry; or is a radical $COR^{4'}$ in which $R^{4'}$ is defined as $R^4$;

$R^5$ and $R^6$ are, independently of one another, hydrogen, $C_1-C_8$-alkyl or $C_6-C_{12}$-aryl.

3. A compound of the formula I as claimed in claim 1, wherein $R^1$ is a radical of the formula II in which R' and R" are, independently of one another, hydrogen or $C_1-C_2$-alkyl;

$R^2$ is hydrogen or $C_1-C_6$-alkyl which is substituted twice by identical or different radicals $R^4$, where $R^4$ is hydroxyl; amino; an amino-acid side-chain; a residue of a natural or unnatural amino acid, imino acid, optionally $N-C_1-C_8$-alkylated or $C_6-C_{14}$-aryl-$C_1-C_8$-alkylated azaamino acid or a dipeptide in which the peptide linkage can be reduced to $NH-CH_2$, and the esters and amides thereof, where free functional groups can optionally be replaced by hydrogen or hydroxymethyl or protected by protective groups customary in peptide chemistry; or is a radical $COR^{4'}$ in which $R^{4'}$ is defined as $R^4$.

4. A compound of the formula I as claimed in claim 3, wherein $R^2$ is methyl which is substituted twice by different radicals $R^4$ and $COR^{4'}$ where $R^4$ and $R^{4'}$ are defined as in claim 3.

5. A compound of the formula I as claimed in claim 1, wherein $R^1$ is a radical of the formula II in which R' and R" are hydrogen, $R^2$ is hydrogen or $C_1-C_6$-alkyl which is substituted once or twice, independently of one another, by $-OH$, $NH_2$, $-COOH$, $-CONH_2$, $-NH-C(NH_2)=NH$, $C_5-C_8$-cycloalkyl, a radical $R^3$ where $R^3$ is $C_6-C_{14}$-aryl which can optionally be substituted by hydroxyl, is a bicyclic 8- to 12-membered heterocyclic aromatic ring which contains as hetero element a nitrogen atom, or a radical $R^4$ where $R^4$ is $NR^5R^6$, a residue of a natural or unnatural amino acid, imino acid, optionally $N-C_1-C_4$-alkylated or $N-C_6-C_{14}$-aryl-$C_1-C_4$-alkylated azaamino acid or a dipeptide, and the amides thereof, or a radical $COR^{4'}$ in which $R^{4'}$ is defined as $R^4$, $R^5$ is hydrogen, $R^6$ is $C_1-C_6$alkyl, and n is 3.

6. A process for preparing a compound of the formula I as claimed in claim 1, which comprises $a_1$) heating compounds of the formula IV

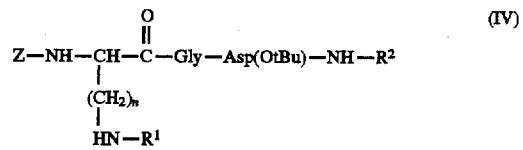

in which Z, is benzyloxycarbonyl and $R^1$, $R^2$ and n have the meanings indicated in claim 1 in tetrahydrofuran under reflux for about 2–3 hours, or $a_2$) condensing compounds of the formula VI and VII

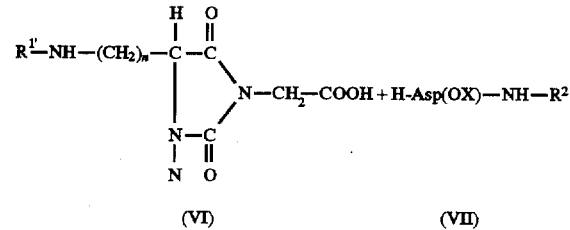

in which $R^{1'}$ is $-C(NH_2)=N-NO_2$ or is defined as $R^1$ above,

X is tBu or Bzl, and $R^2$ and n have the meanings described above, by general methods of peptide chemistry, and b) converting the hydantoins of the general formula V which have been produced by process steps $a_1$) or $a_2$) above

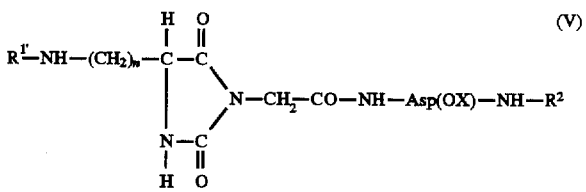

by catalytic hydrogenation and/or acid elimination of the protective groups into the compounds of the formula I according to the invention.

7. A pharmaceutical composition comprising a compound of the formula I as claimed in claim 1 or a physiologically acceptable salt thereof, and a physiologically acceptable vehicle.

8. A pharmaceutical composition as claimed in claim 7 for inhibiting platelet aggregation.

9. A pharmaceutical composition as claimed in claim 7 for inhibiting the binding of osteoclasts to the surface of bone.

10. A method of treatment for inhibiting platelet aggregation comprising administering to a subject in need of such treatment an effective amount of a compound of the formula I as claimed in claim 1, or a physiologically acceptable salt thereof.

11. The method as claimed in claim 10, wherein the subject is a mammal.

12. A method of treatment for inhibiting the binding of osteoclasts to the surface of bone comprising administering to a subject in need of such treatment an effective amount of a compound of the formula I as claimed in claim 1, or a physiologically acceptable salt thereof.

13. The method as claimed in claim 12, wherein the subject is a mammal.

* * * * *

UNITED STATES PATENT AND TRADEMARK OFFICE
CERTIFICATE OF CORRECTION

PATENT NO. : 5,686,421
DATED : November 11, 1997
INVENTOR(S) : Wolfgang KONIG et al.

It is certified that error appears in the above-identified patent and that said Letters Patent is hereby corrected as shown below:

Claim 1, column 20, line 38, "$C_8-C_{14}$-aryl-$C_1-C_8$-alkyl" should read --$C_6-C_{14}$-aryl-$C_1-C_8$-alkyl--.

Claim 1, column 21, line 1, "$R^5$" should read --$R^6$--.

Claim 5, column 22, line 7, "$C_1-C_6$alkyl" should read --$C_1-C_6$-alkyl--.

Signed and Sealed this

Third Day of November, 1998

Attest:

*Attesting Officer*

BRUCE LEHMAN
*Commissioner of Patents and Trademarks*